(12) United States Patent
Krall

(10) Patent No.: US 7,828,439 B2
(45) Date of Patent: Nov. 9, 2010

(54) SYSTEM AND METHOD FOR MEASURING FIXATION DISPARITY AND PROPRIOCEPTIVE MISALIGNMENT OF THE VISUAL SYSTEM

(76) Inventor: Jeffrey P. Krall, 1415 N. Sanborn Blvd., Mitchell, SD (US) 57301

( * ) Notice: Subject to any disclaimer, the term of this patent is extended or adjusted under 35 U.S.C. 154(b) by 93 days.

(21) Appl. No.: 12/321,440

(22) Filed: Jan. 21, 2009

(65) Prior Publication Data

US 2009/0185137 A1    Jul. 23, 2009

Related U.S. Application Data

(60) Provisional application No. 61/022,418, filed on Jan. 21, 2008.

(51) Int. Cl.
*A61B 3/00* (2006.01)
*A61B 3/02* (2006.01)
*G02C 7/06* (2006.01)

(52) U.S. Cl. .................. 351/246; 351/239; 351/170

(58) Field of Classification Search .......... 351/239, 351/240, 241, 242, 246, 159, 168, 170
See application file for complete search history.

(56) References Cited

U.S. PATENT DOCUMENTS 7,104,647 B2 *  9/2006  Krall .................... 351/170

\* cited by examiner

*Primary Examiner*—Jack Dinh
(74) *Attorney, Agent, or Firm*—Wood, Phillips, Katz, Clark & Mortimer

(57) ABSTRACT

In accordance with the invention there is disclosed a method for determining the amount of prism needed to be placed in spectacle lenses to correct ones fixation disparity and or proprioceptive misalignment, wherein target objects viewed by each eye will be perceived to be at optical infinity and the objects to be viewed by each eye are seen separately but also simultaneously, the method comprising: adding Base Out prism in a smooth and continuous manner until the target objects jump together, switch sides or are suppressed; decreasing Base Out prism and thereafter continuing to add Base In prism until the target objects return to their original position; and recording amount of prism needed to achieve the target objects returning to their original position.

18 Claims, 2 Drawing Sheets

SYSTEM AND METHOD FOR MEASURING FIXATION DISPARITY AND PROPRIOCEPTIVE MISALIGNMENT OF THE VISUAL SYSTEM

CROSS REFERENCE TO RELATED APPLICATIONS

This application claims priority of U.S. application No. 61/022,418, filed Jan. 21, 2008.

FIELD OF THE INVENTION

This invention relates to vision correction and, more particularly, to measuring fixation disparity and proprioceptive misalignment of the visual system.

BACKGROUND OF THE INVENTION

The optical system of the human eye uses numerous muscles as well as central and peripheral cues while focusing on objects both near and far. There are many responses involved in changing focus from distance to near as well as fixating on an object at a set distance.

While focusing on near objects, such as a computer, the visual system must converge on the object being viewed. After a period of time the eyes may become strained, feel dry, or start to blur. It is believed that the visual system after prolonged near activity may experience a proprioceptive lag as to where the object being viewed is located. In other words the perceived distance of the object being viewed is different than its actual location. When this occurs the visual system in many instances develops eye strain due to the constant cortical supervision to maintain binocularity. Fatigue, eyestrain, dry eye, along with other symptoms are the results of the misalignment or eyes.

While the use of this system and method is intended to be used with any ophthalmic lens, it is particularly relevant to the ophthalmic lenses described in U.S. Pat. No. 7,104,647, "Multi-focal ophthalmic lens with base in prism". This invention is intended to compliment U.S. Pat. No. 7,104,647 by determining if additional prism is needed for the distance portion of the ophthalmic lens.

SUMMARY OF THE INVENTION

The present invention relates to a method of measuring ones fixation disparity in order to determine the prismatic power to be placed in an ophthalmic lens. The present invention also relates to method for measuring ones proprioceptive lag or adaptation.

The intent of this invention is to measure the amount of fixation disparity and proprioceptive lag which will help alleviate ones eyestrain symptoms.

There is disclosed in accordance with one aspect of the invention an improvement in an ophthalmic lens, either single vision or multifocal, wherein either vertical and/or horizontal prism is introduced in the distance portion of the lens.

It is a feature of this invention that fixation disparity can be measured in a portable hand held device.

It is another feature of this invention that the viewing distance will simulate optical infinity.

Is a further feature of this invention that the viewing distance may be adjusted when needed to simulate near vision.

It is still another feature of this invention that peripheral fusion is maintained while central fusion is absent.

The present invention provides a method to accurately measure the minimal amount of prism to be placed in an ophthalmic lens in order to alleviate fixation disparity or ones proprioceptive misalignment.

DETAILED DESCRIPTION OF THE INVENTION

Figure 1:
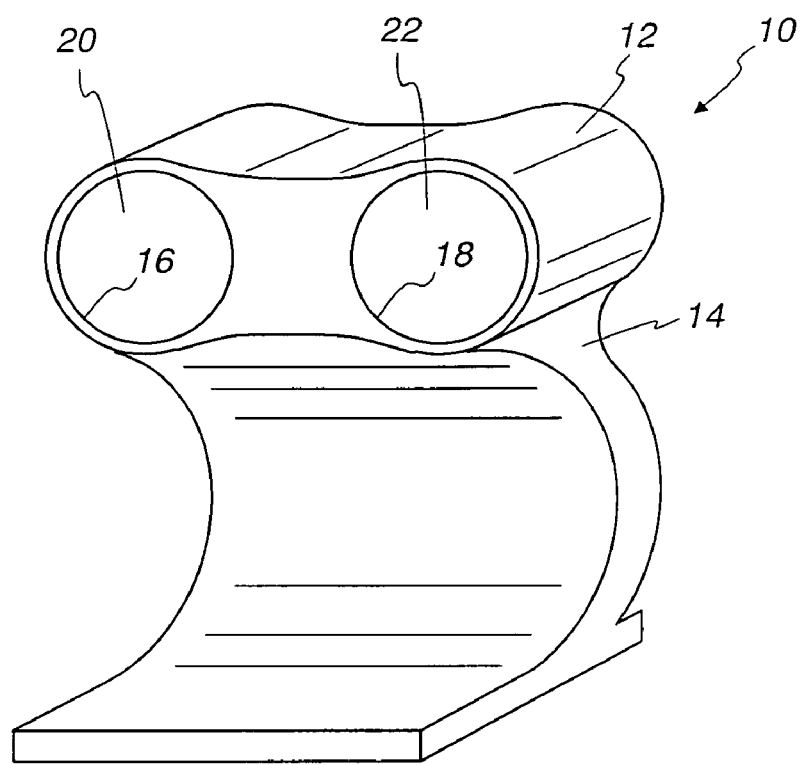
FIG. 1 is a conceptual view of an exemplary portable table top device in accordance with the invention.

The present invention comprises a vision testing apparatus designed to measure fixation disparity and proprioceptive lag of the visual system. The intent of this apparatus is to determine the amount of prism, either vertically and/or horizontally, to be placed in a spectacle lens. This apparatus is intended to be used for children and adults with or without a spectacle or contact lens correction. Advantageously, the apparatus is a self contained portable apparatus either hand held, or table mount with movable ocular elements to accommodate one's pupillary distance. The apparatus will simulate optical infinity while viewing target letters and/or objects which may vary in size, shape and color. The foveal targets are intended to be viewed separately by each eye in which the right eye can see the right central target and the left eye can see left central target, but the right central target cannot be seen by the left eye and the left central target cannot be seen by the right eye (lack of foveal binocularity). While there is a lack of central binocularity, this apparatus allows for peripheral binocularity in which the borders and or outside targets (outside of the central vision) can be viewed by both right and left eyes at the same time. This apparatus will allow for peripheral fusion while central fusion will be absent.

While a viewer is looking into the apparatus, base out prism is added thereby causing the eyes to converge. This convergence will cause the viewer to notice one of three possible occurrences. The targets will run together (superimposed), or the targets will switch sides (horizontal misalignment) or the targets will disappear (suppression). If any misalignment occurs either vertically or horizontally, the examiner will have the viewee align the letters or objects with a built in measuring device. This will be done via decreasing the induced base out prism allowing the targets to return to the original location. The amount of prism recorded will be the minimal amount to keep the targets aligned either vertically and/or horizontally.

Another feature of this invention is the use of a multiple pinhole occluder which will be alternated over one eye and then the other causing a break in fusion. The use of the pinhole occluder will be to control the accommodative convergent response by decreasing the blur and the stimulation of accommodation and the accommodative convergence mechanism. This will allow for a more accurate measurement of the misalignment of the eyes. While viewing a central target the instrument will add prism either: Base Out, Base Up, Base In, or Base Down to reduce perceived movement of the targets. This will be recorded and be prescribeable for a final spectacle correction.

Another feature of this invention is that it employs the use of a single target which again will be seen at optical infinity. While the subject is viewing the target under binocular conditions with no septum in place and foveal fusion present a pinhole occluder will be alternated between the right and left eyes at a rate that may be varied by the examiner. Prism either horizontally or vertically will then be added until no moment is noted by the subject.

Another feature of this invention is that it may employ the methods discussed herein, but instead of performing the test at optical infinity it would be done simulating a near target or one at any distance between.

FIG. 1 is a conceptual view of an exemplary portable table top apparatus 10 in accordance with the invention. The apparatus 10 includes a housing 12 atop a stand 14. The housing includes openings 16 and 18 covered by lenses 20 and 22, respectively, for viewing by a user. The apparatus resembles conventional binoculars with a built-in stand.

Figure 2:
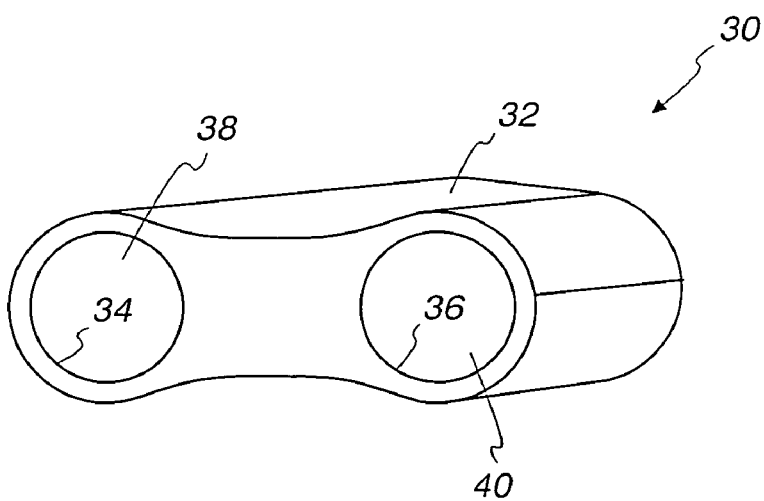
FIG. 2 is a conceptual view of an exemplary hand held device in accordance with the invention.

FIG. 2 is a conceptual view of an exemplary hand held apparatus 30 in accordance with the invention. The apparatus 30 includes a hand held housing 32. The housing 32 includes openings 34 and 36 covered by lenses 38 and 40, respectively, for viewing by a user. The apparatus 30 resembles conventional binoculars.

Figure 3:
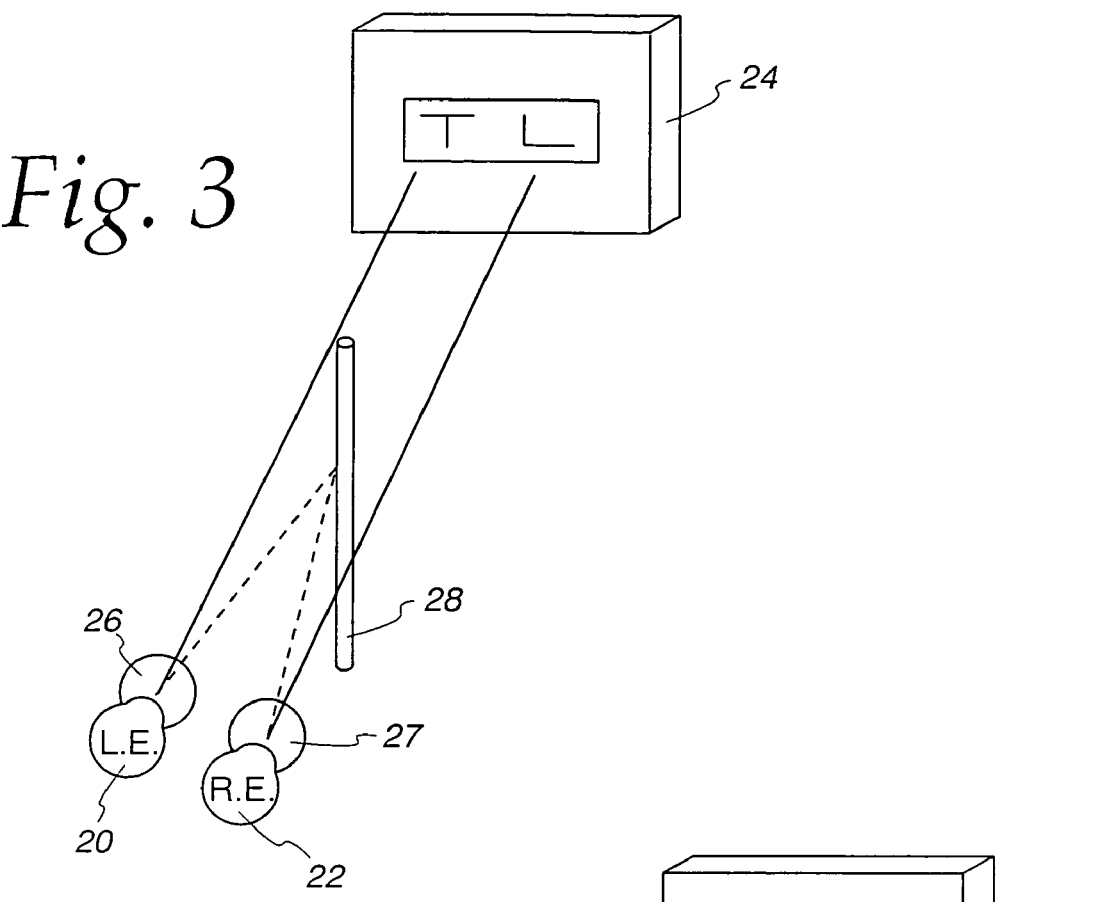
FIG. 3 is a schematic representation of the devices of FIG. 1 or 2.

FIG. 3 is a schematic representation of the apparatus 10 of FIG. 1. This schematically represents what the viewer would see while looking into the apparatus 10. For convenience, only the apparatus 10 is described in detail below, it being understood that the apparatus 30 operates similarly, except for being hand held.

The apparatus 10 includes a viewing target 24 in the housing 12 opposite the lenses 20 and 22. The target 24 includes objects in the form of representative letters T and L. A prismatic measuring device, represented at 26 and 27, one for each eye, may comprise a Risley prism or the like. As is known, a Risley prism comprises a type of dispersing prism used to test ocular convergence in ophthalmology. It typically consists of thin prisms mounted so that they can be rotated simultaneously in opposite directions. The prisms may be rotated manually or electro-mechanically, as is known. Such a Risley prism provides an indication, either visually or by electrical signal, representing ocular convergence or divergence.

FIG. 3 illustrates how only the right eye (R.E) viewed through the lens 22 sees the letter L and the left eye (L.E.) viewed through the lens 20 sees the letter T, represented by solid lines. The dashed lines depict how the eyes are blocked from viewing opposite sides of the target 24. This is accomplished through either a mechanical or virtual septum 28 depicted halfway between the lenses 20 and 22 and the target 24 which is perceptually viewed at infinity.

Figure 4:
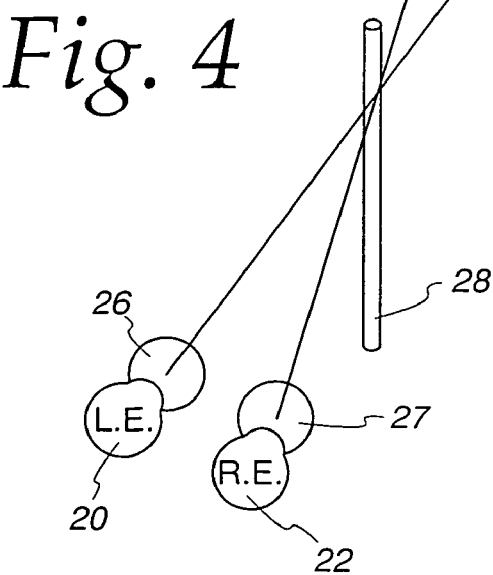
FIG. 4 is a schematic representation, similar to FIG. 3, depicting what the viewer may experience when there is a proprioceptive misalignment or fixation disparity.

FIG. 4 is a schematic representation, similar to FIG. 3, depicting what the viewer may experience when there is a proprioceptive misalignment or fixation disparity, where the objects L and T appear to switch sides. The solid lines show how the right eye now sees the letter L and the left eye sees the letter T.

FIGS. 3 & 4 are shown in a time lapse as to what may occur when prism is added to measure ones proprioceptive misalignment, as discussed above.

Using the prismatic measuring apparatus 10 the periphery target objects as seen by both eyes may be varied by size, color and/or illumination. The central targets separated by the septum 28 either physically or perceptually within this apparatus may be adjusted in size, color and illumination. The objects viewed by each eye will be perceived to be at optical infinity. The objects to be viewed by each eye will be seen separately but also simultaneously.

Using the adjustable prisms 26 and 27, Base Out Prism is added in a smooth and continuous manner until the images jump together; switch sides or suppression is noted, such as in FIG. 4. Then slowly a decrease in Base Out prism is started until Zero prism diopters are present and then continuing to add Base In prism at the same rate until the images return to their original positions, as in FIG. 3. When the targets are in positions which the subject perceives are back to the original starting position, that being the right eye sees the right target on the right side and the left eye sees the left target on the left side, and not superimposed upon each other, the amount of prism needed to achieve this is recorded. This amount of prism can then be used to compliment U.S. Pat. No. 7,104,647 by determining if additional prism is needed for the distance portion of the ophthalmic lens. The goal is the minimal amount of Base In prism needed to effectively keep the images separate.

The present invention further comprises a method for determining the amount of prism needed to be placed in ophthalmic lenses to correct ones fixation disparity and or proprioceptive misalignment. The display medium to be used (target comprising objects or letters) is controlled by the examiner. The periphery targets seen by both eyes may be varied by size, color and illumination. The central targets may be adjusted in size, color and the illumination. The objects viewed by each eye will be perceived to be at optical infinity. The objects to be viewed by each eye will be seen separately by but also simultaneously. Base Out Prism is added in a smooth and continuous manner until the images jump together, switch sides or suppression is noted. Then slowly a decrease in Base Out prism is started until Zero prism diopters are added, then continuing to add Base In prism at the same rate until the images return to their original positions. When the targets in which the subject perceives are back to the original starting position that being the right eye sees the right target on the right side and the left eye sees the left target on the left side, and not superimposed upon each other, the amount of prism needed to achieve this is recorded. The goal is the minimal amount of Base In prism needed to effectively keep the images separate.

In accordance with the invention the letters or objects to be used may vary in size, shape and color. The letters used are consistent with snellen letters used in an optometric practice. The letters used may subtend between 1 and 5 minutes of arc and may range in size from 20/100 to 20/20.

The method of measuring fixation disparity is achieved by viewing objects monocularly under binocular conditions. In order to promote peripheral fusion a border varying in color and brightness is used. The letters are kept separate by a septum separating right from left eyes. The border around the letters will be seen by both eyes peripherally and brightness and color may be varied. Prism is measured in diopters. The prismatic power vertically and horizontally will be similar to a Risley prism or the equivalent thereof, in order to introduce prism in a continuous manner. The amount of prism recorded will be the minimal amount to keep the objects or letters apart.

I claim:

1. A method for determining the amount of prism needed to be placed in ophthalmic lenses to correct ones fixation disparity and or proprioceptive misalignment, wherein target objects viewed by each eye will be perceived to be at optical infinity and the objects to be viewed by each eye are seen separately but also simultaneously, the method comprising:

adding Base Out prism in a smooth and continuous manner until the target objects jump together, switch sides or are suppressed;

decreasing Base Out prism and thereafter continuing to add Base In prism until the target objects return to their original position; and recording amount of prism needed to achieve the target objects returning to their original position.

2. The method of claim 1, wherein the target objects have a select size, shape and color.

3. The method of claim 2, wherein the target objects comprise snellen letters.

4. The method of claim 3, wherein the letters subtend between 1 and 5 minutes of arc.

5. The method of claim 2, wherein the target objects range in size from 20/100 to 20/20.

6. The method of claim 1 wherein measuring fixation disparity is achieved by viewing objects monocularly under binocular conditions and wherein a border varying in color and brightness is used to promote peripheral fusion.

7. The method of claim 6, wherein the target objects are kept separate by a septum separating right from left eyes and wherein the border is seen by both eyes.

8. The method of claim 1, wherein prism is measured in diopters.

9. The method of claim 1, wherein the prismatic power vertically and horizontally will be similar to a Risley prism, in order to introduce prism in a continuous manner.

10. The method of claim 1 wherein the amount of prism recorded is a minimal amount to keep the target objects apart.

11. The method of claim 1 in which wherein target objects viewed by each eye are alternatively set for a near target.

12. An apparatus for determining the amount of prism needed to be placed in ophthalmic lenses to correct ones fixation disparity and or proprioceptive misalignment comprising:

a housing having openings and target objects that when viewed by each eye will be perceived to be at optical infinity and the target objects to be viewed by each eye are seen separately but also simultaneously; and an adjustable prism disposed between the openings and the target objects and being operable so that a user adds Base Out prism in a smooth and continuous manner until the target objects jump together, switch sides or are suppressed, and subsequently decreasing Base Out prism and thereafter continuing to add Base In prism until the target objects return to their original position to enable the user to determine amount of prism needed to achieve the target objects returning to their original position.

13. The apparatus of claim 12, wherein the target objects have a select size, shape and color.

14. The apparatus of claim 13, wherein the target objects comprise snellen letters.

15. The apparatus of claim 14, wherein the letters subtend between 1 and 5 minutes of arc.

16. The apparatus of claim 12, wherein the target objects range in size from 20/100 to 20/20.

17. The apparatus of claim 12, wherein the target objects are kept separate by a septum separating right from left eyes.

18. The apparatus of claim 12, wherein the adjustable prism comprises a Risley prism, in order to introduce prism in a continuous manner.

* * * * *